United States Patent [19]

Miyazaki et al.

[11] Patent Number: 5,239,319
[45] Date of Patent: Aug. 24, 1993

[54] MICROPUMP SUPERVISORY CONTROL

[75] Inventors: Hajime Miyazaki; Masaaki Handa; Taisuke Uehara; Tsukasa Muranaka, all of Suwa, Japan

[73] Assignee: Seiko Epson Corporation, Tokyo, Japan

[21] Appl. No.: 858,783

[22] Filed: Mar. 27, 1992

Related U.S. Application Data

[62] Division of Ser. No. 644,704, Jan. 23, 1991.

[51] Int. Cl.5 .............................................. G08B 19/00
[52] U.S. Cl. .................................... 340/679; 310/316; 310/317; 310/328; 340/309.4; 340/691; 417/63
[58] Field of Search ............ 340/679, 540, 691, 309.4, 340/309.15; 417/63, 413, 322; 310/328, 316, 317

[56] References Cited

U.S. PATENT DOCUMENTS

| | | | |
|---|---|---|---|
| 3,290,669 | 12/1966 | Mews | 340/679 |
| 4,560,979 | 12/1985 | Rosskopf | 340/540 |
| 4,602,249 | 7/1986 | Abbott | 340/679 |
| 4,649,886 | 3/1987 | Igashira et al. | 123/498 |
| 4,660,027 | 4/1987 | Davis | 340/691 |
| 4,911,616 | 3/1990 | Laumann, Jr. | 417/413 |

FOREIGN PATENT DOCUMENTS 112678  4/1990  Japan.

Primary Examiner—Glen R. Swann, III
Attorney, Agent, or Firm—Gregory D. Ogrod

[57] ABSTRACT

A micropump supervisory control method and apparatus having various functions, such as annunciation and safety measures. The control method and apparatus accurately control trace discharge rates through adjustment of the number and frequency of driving pulses for a piezoelectric valve element. In addition, the control method provides discharge, life-prediction and life-expiration warning, and operation acknowledge alarms and annunciations while driving the micropump, each having a predetermined sounding pattern. Micropump functions are also inhibited when a power source is reconnected.

20 Claims, 13 Drawing Sheets

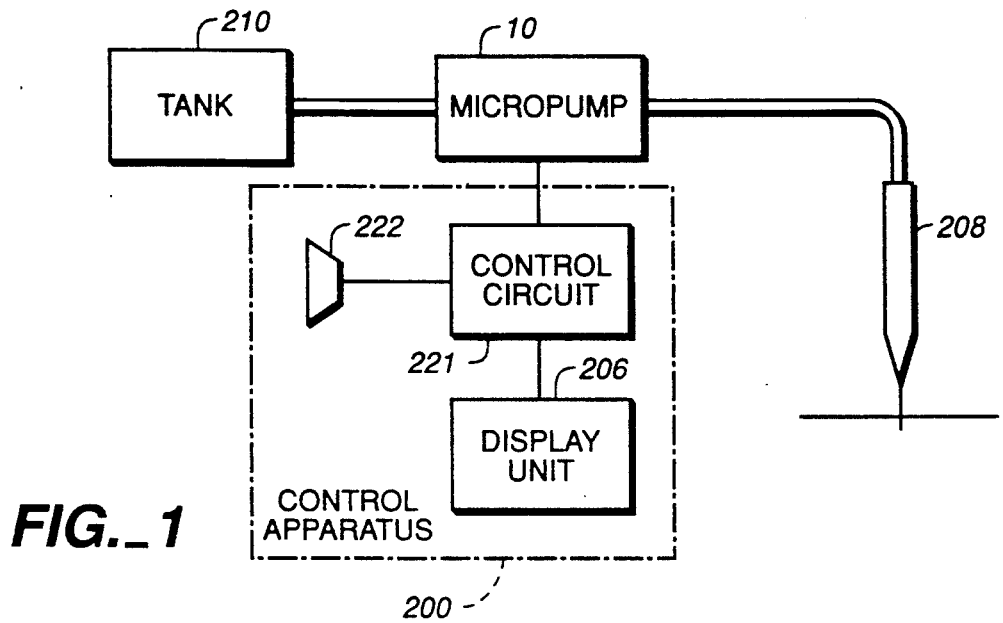
FIG._1
| SWITCH | MODE - 0 , MODE - 3 | MODE - 1 | MODE - 2 |
|--------|---------------------|----------|----------|
| A | INEFFECTIVE | PULSE CHECK | INEFFECTIVE |
| B | INEFFECTIVE | ALARM TEST HEARING | INEFFECTIVE |
| C | INEFFECTIVE | GENERATION OF PIEZOELECTRIC ELEMENT DRIVING PULSES ON/OFF | |
| D | INEFFECTIVE | STOP SOUNDING OF OPERATION ACKNOWLEDGE AND ALARM AL$_1$ | |
| E | INEFFECTIVE | SELECTION OF PIEZOELECTRIC ELEMENT DRIVING PULSE OUTPUT PATTERN | |
FIG._3

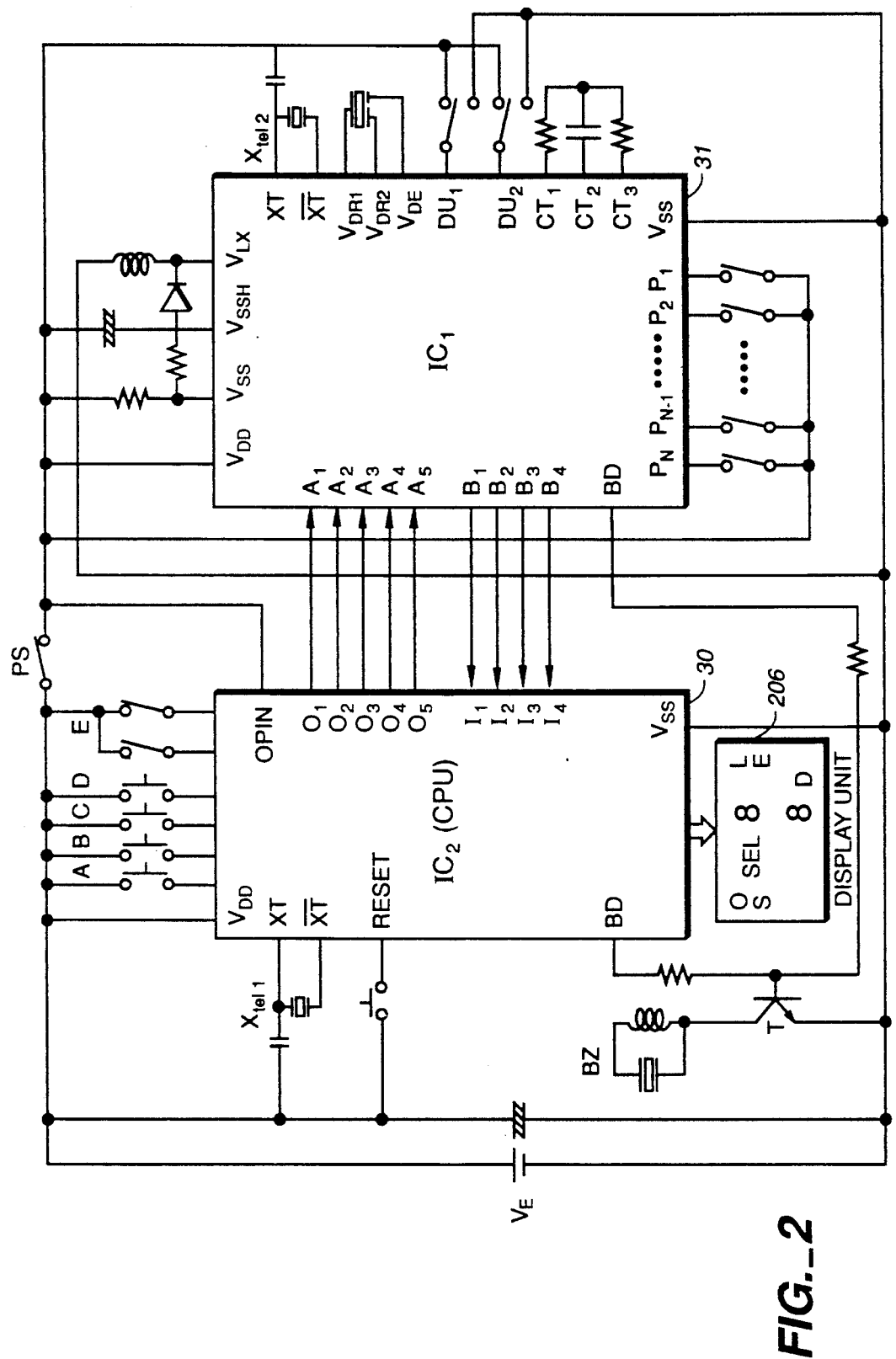
FIG._2

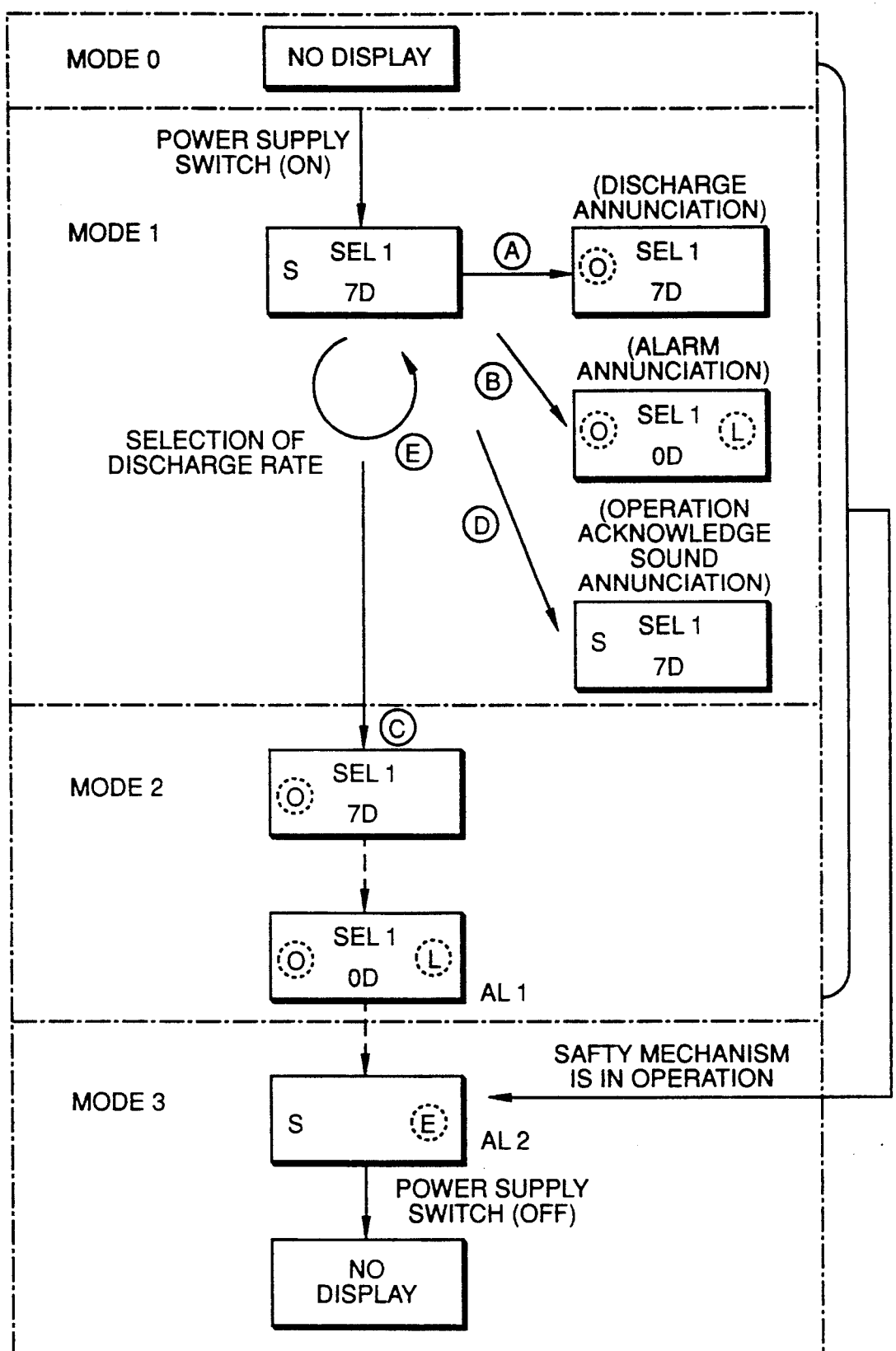
FIG._4

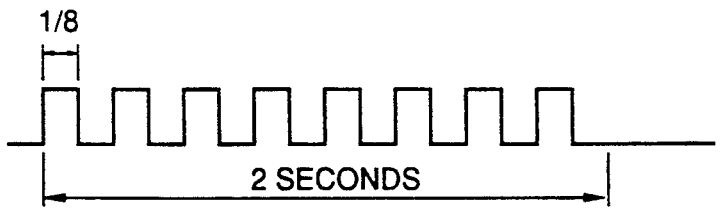
FIG._5
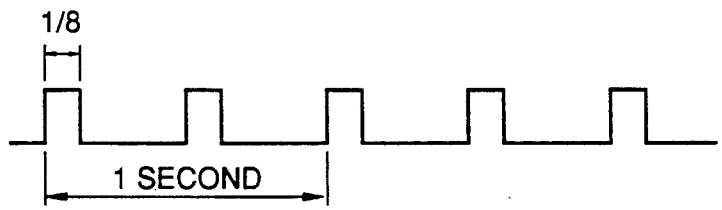
FIG._6
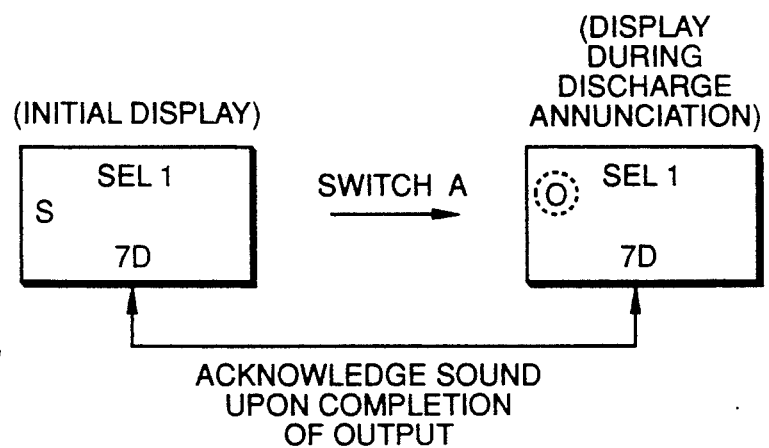
FIG._7
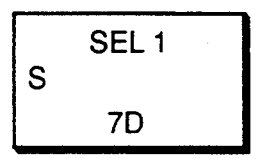
FIG._8
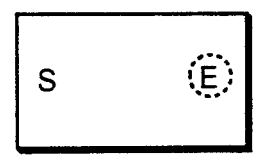

FIG._9 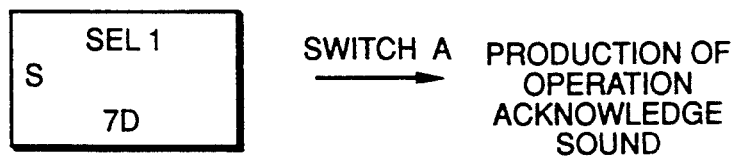
FIG._10 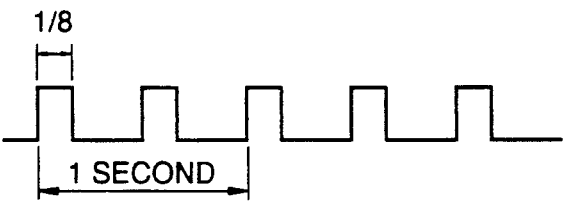
FIG._11 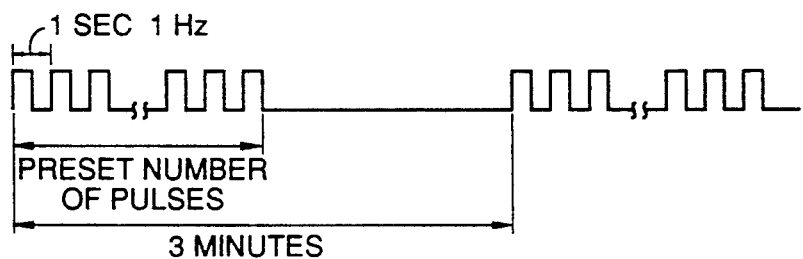
FIG._12 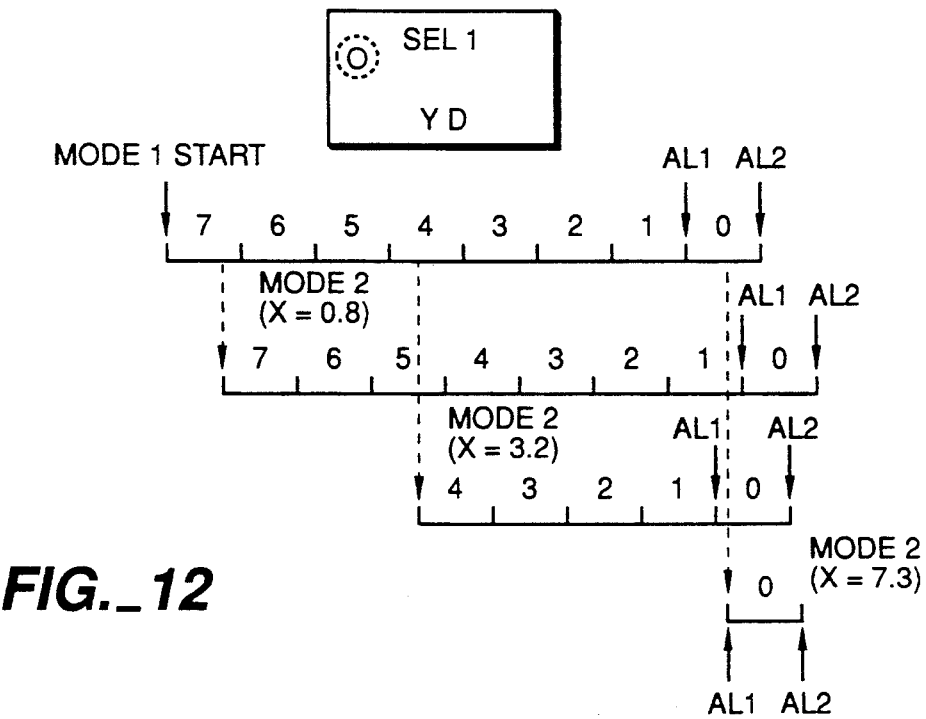

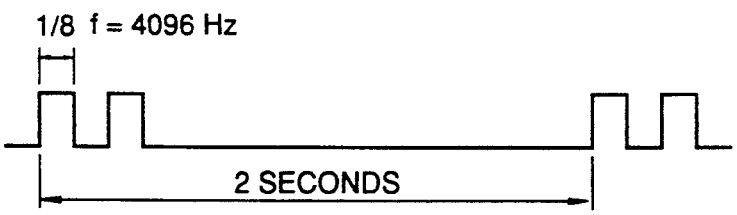
FIG._13
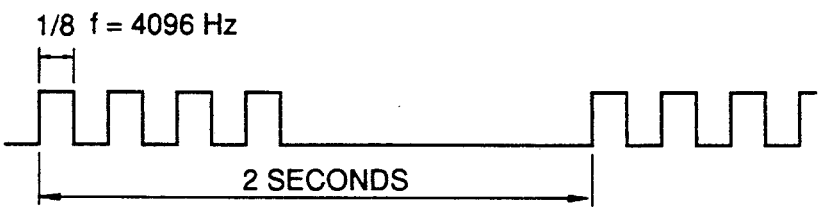
FIG._14
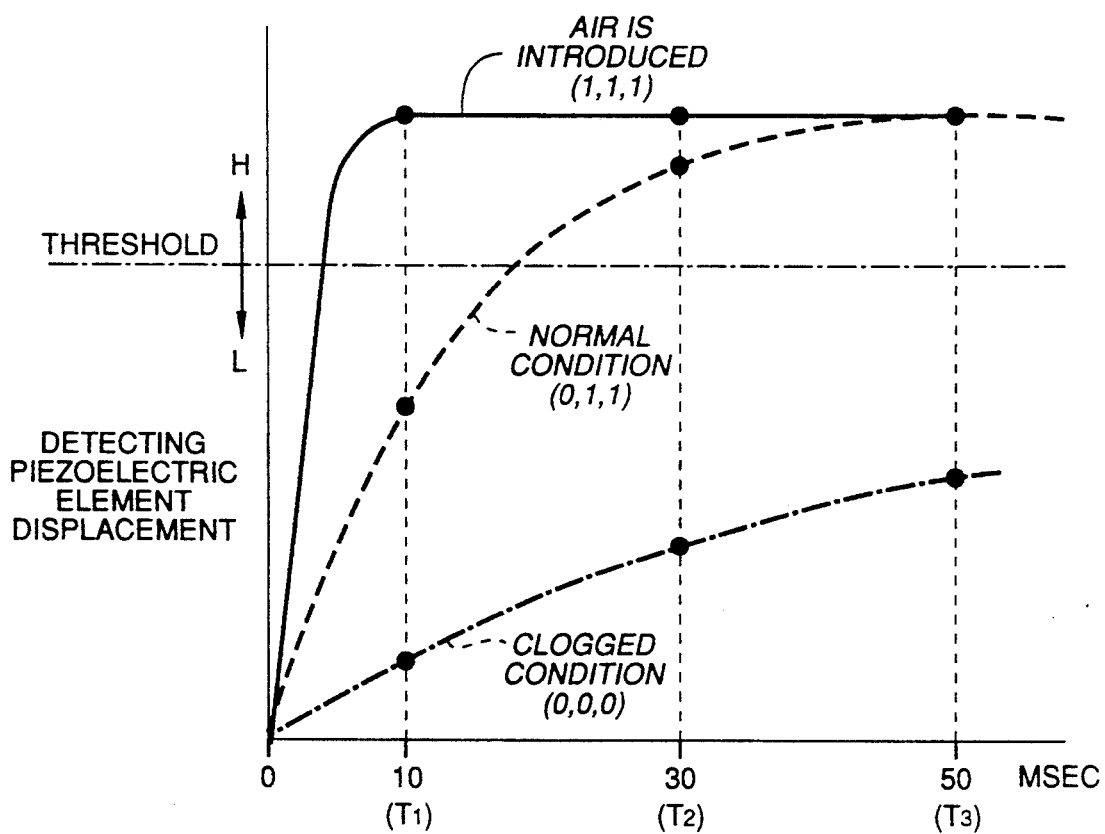
FIG._15

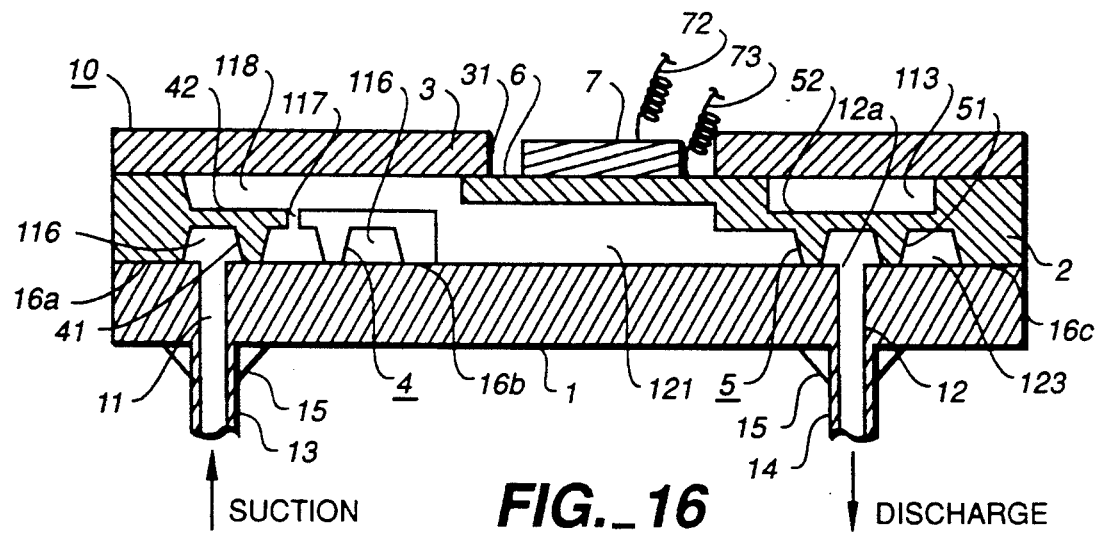
FIG._16
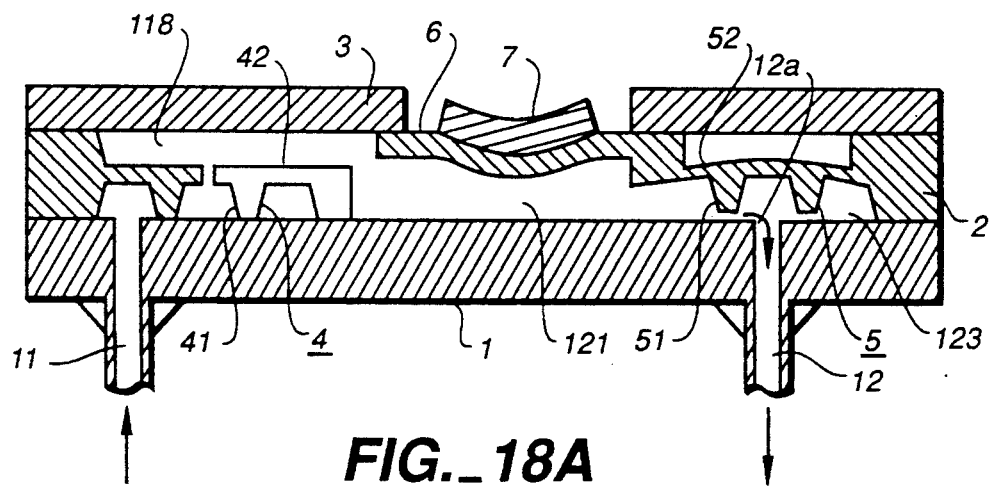
FIG._18A
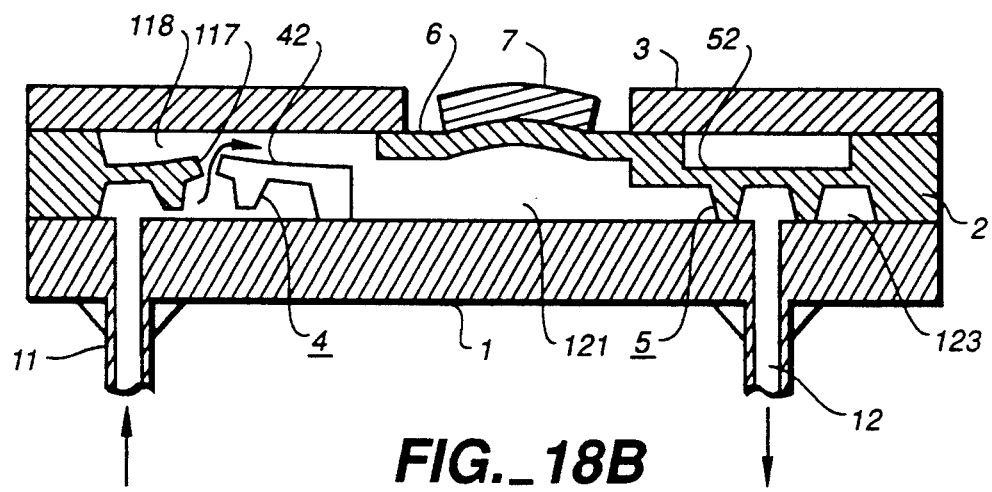
FIG._18B

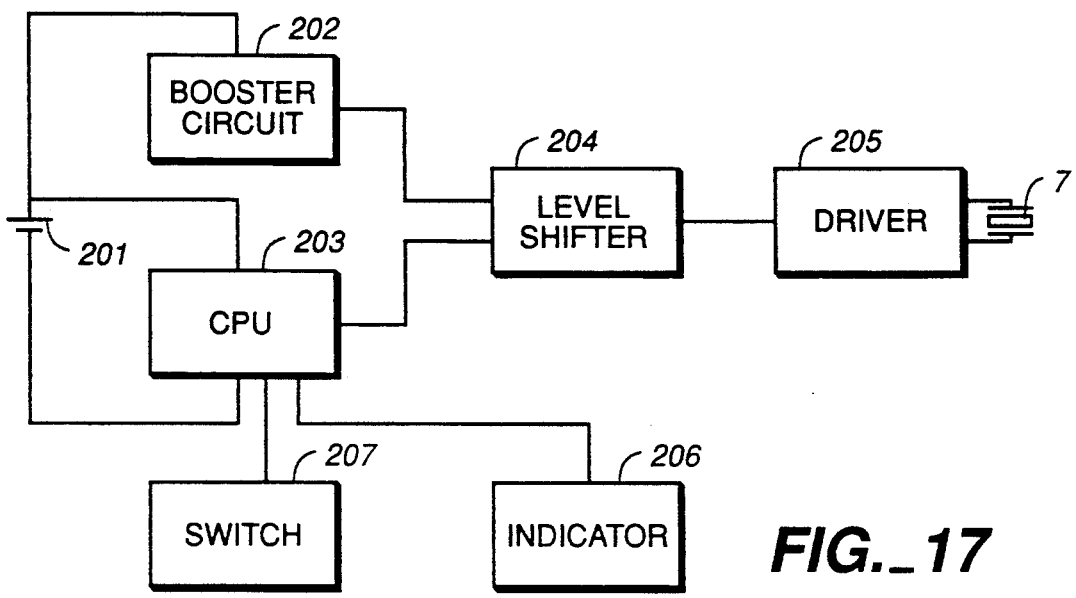
FIG._17
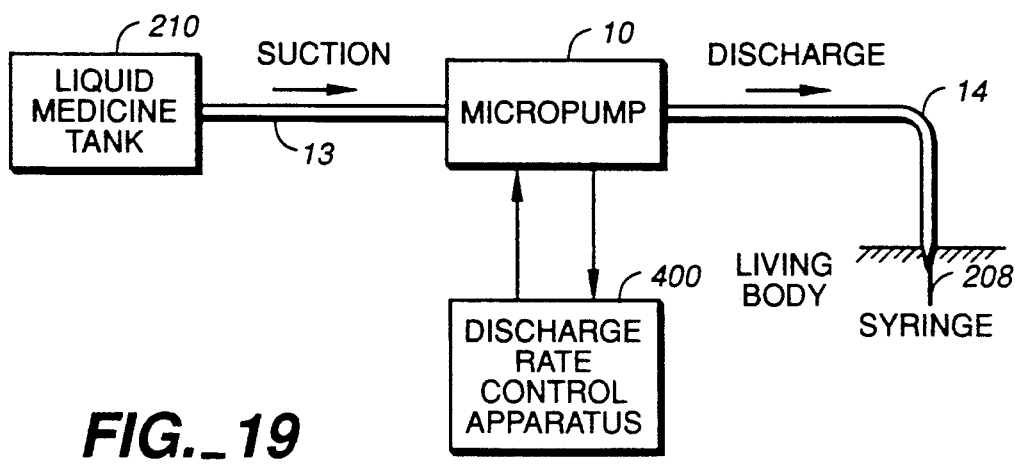
FIG._19

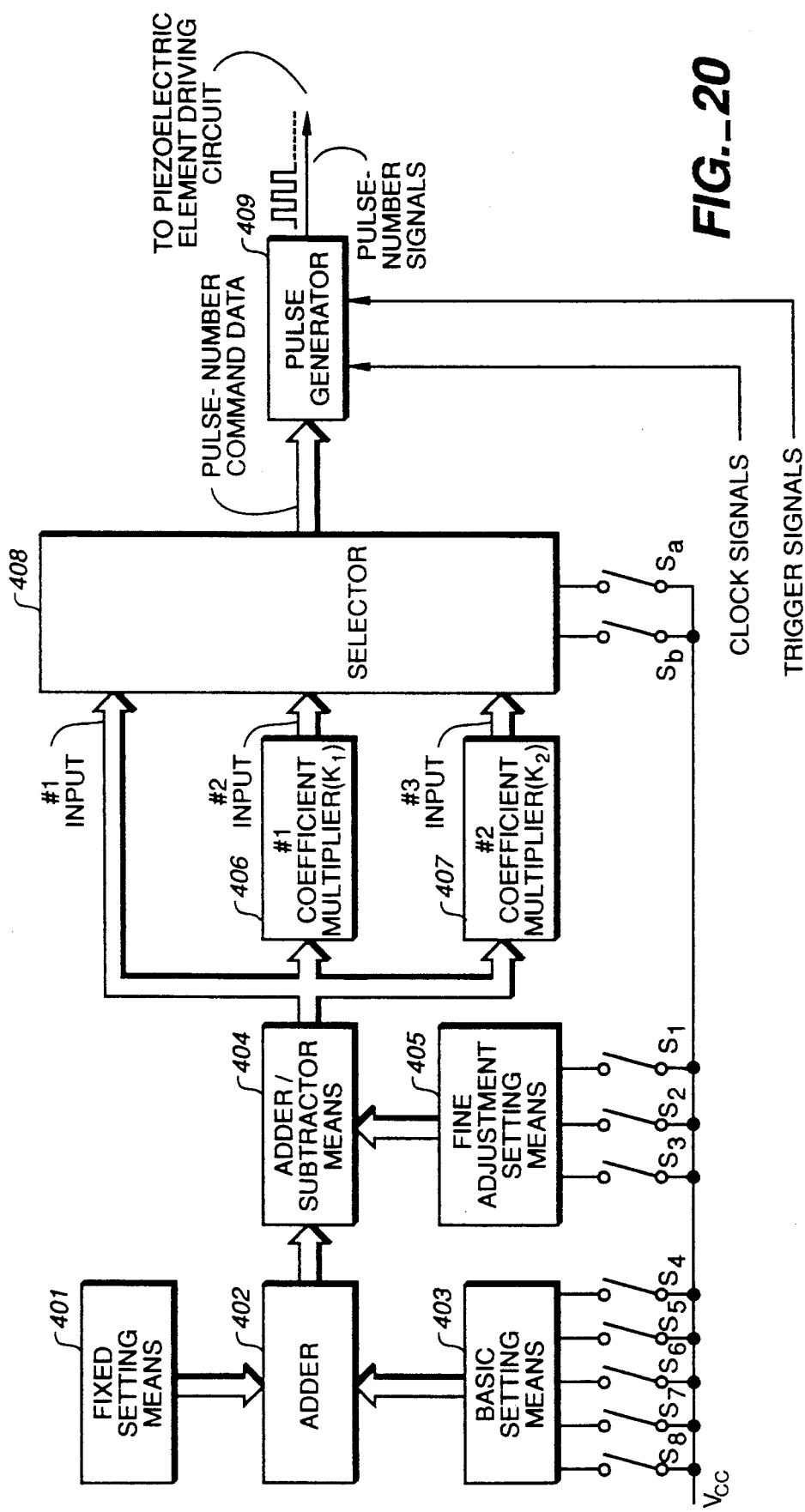
FIG._20

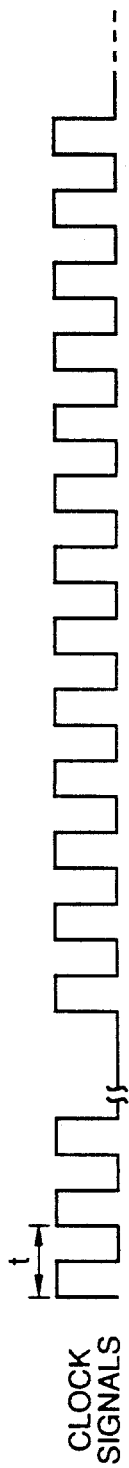
FIG._21A CLOCK SIGNALS
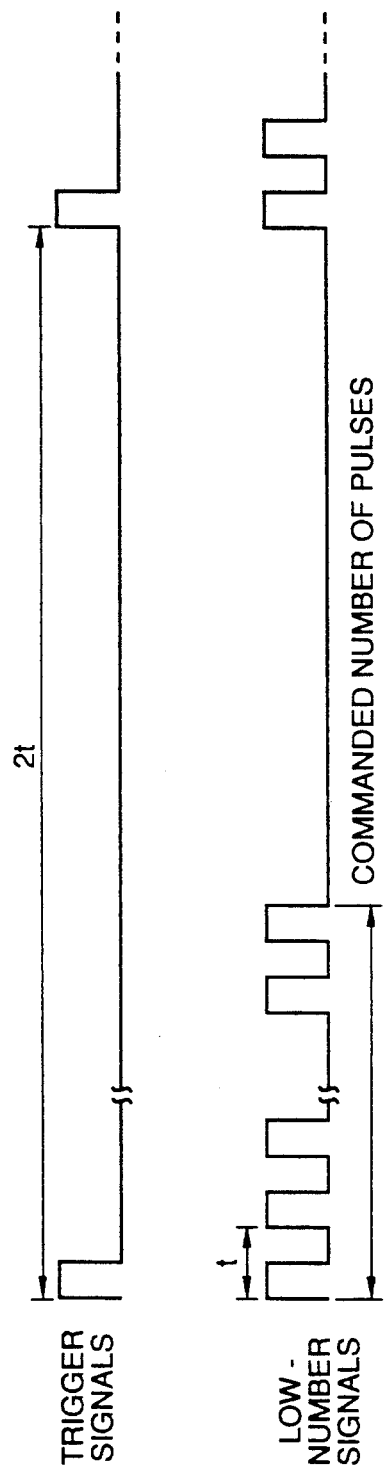
FIG._21B TRIGGER SIGNALS
FIG._21C LOW-NUMBER SIGNALS
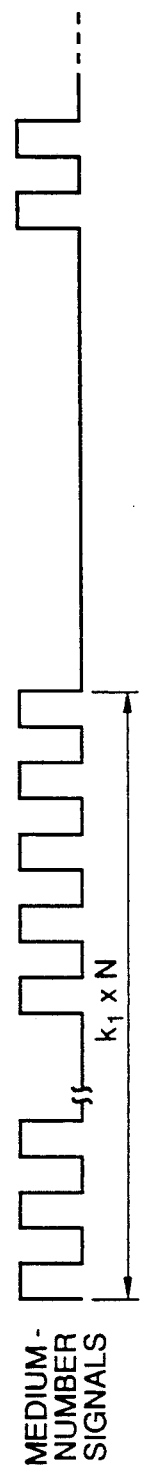
FIG._21D MEDIUM-NUMBER SIGNALS
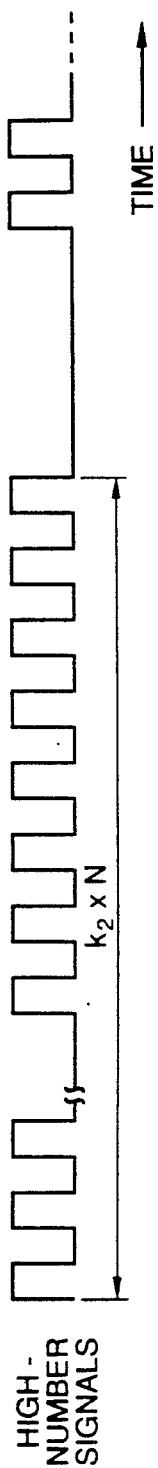
FIG._21E HIGH-NUMBER SIGNALS

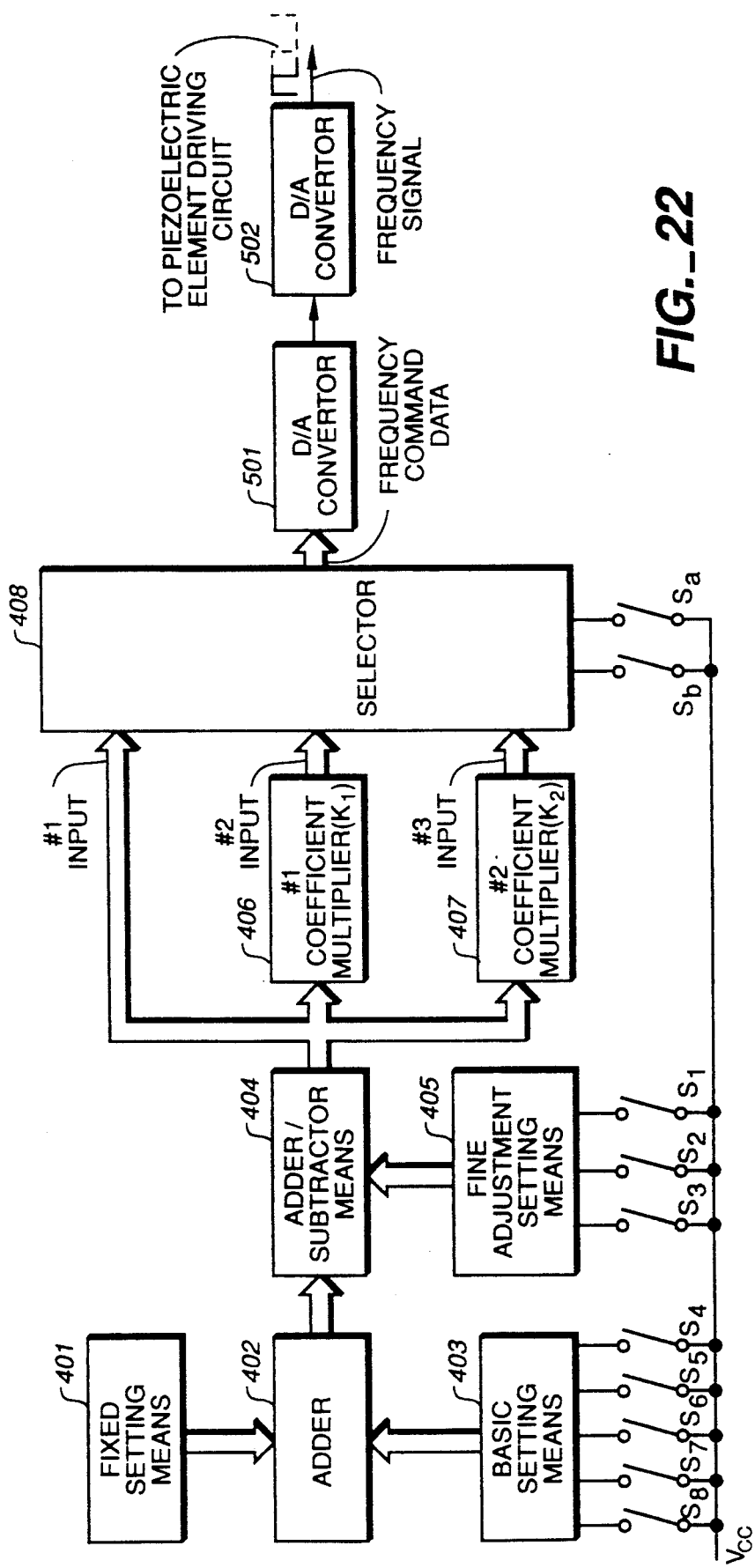
FIG._22

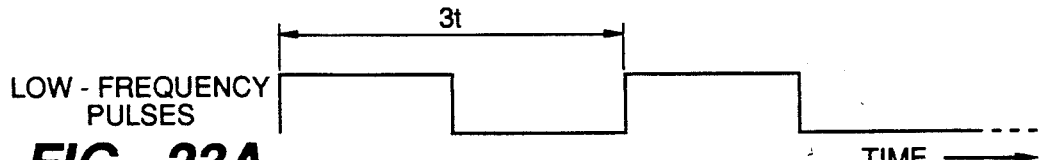
FIG._23A
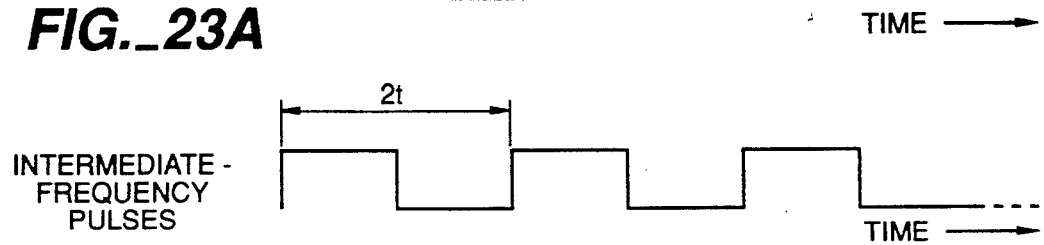
FIG._23B
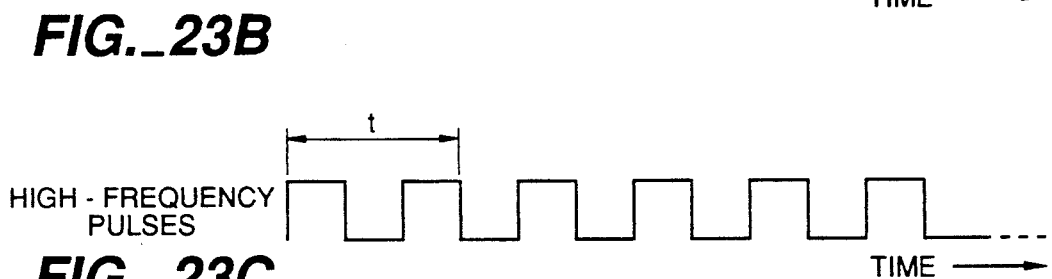
FIG._23C
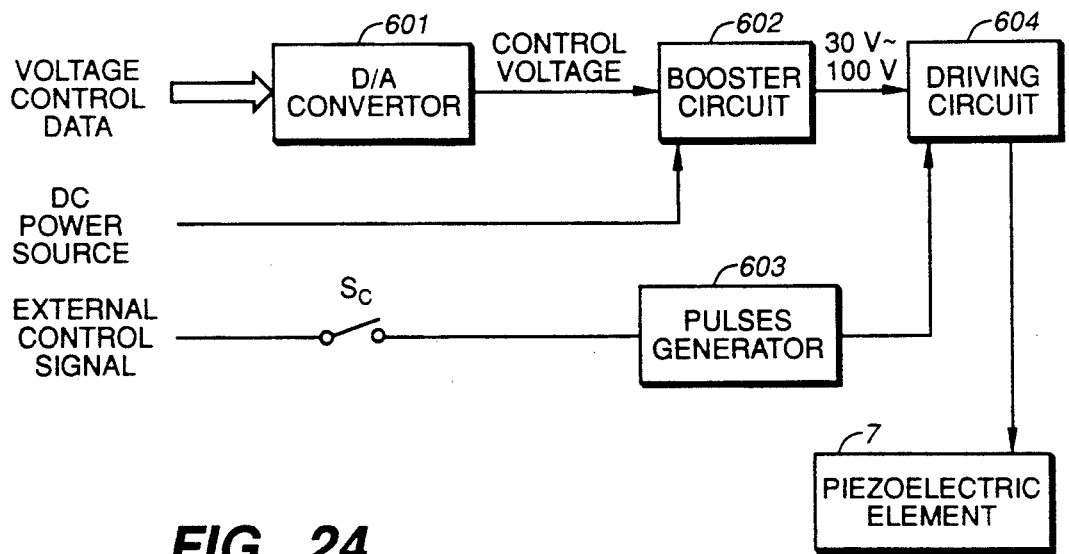
FIG._24

FIG._25A LOW-VOLTAGE PULSES 30V TIME
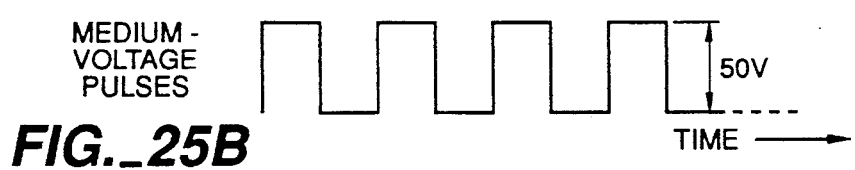
FIG._25B MEDIUM-VOLTAGE PULSES 50V TIME
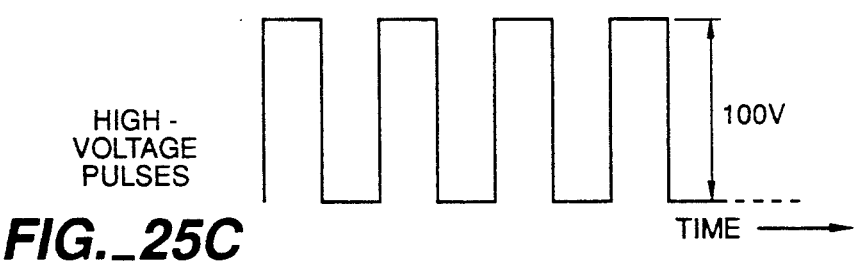
FIG._25C HIGH-VOLTAGE PULSES 100V TIME
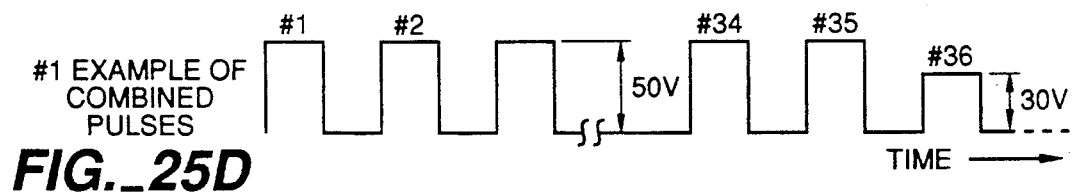
FIG._25D #1 EXAMPLE OF COMBINED PULSES
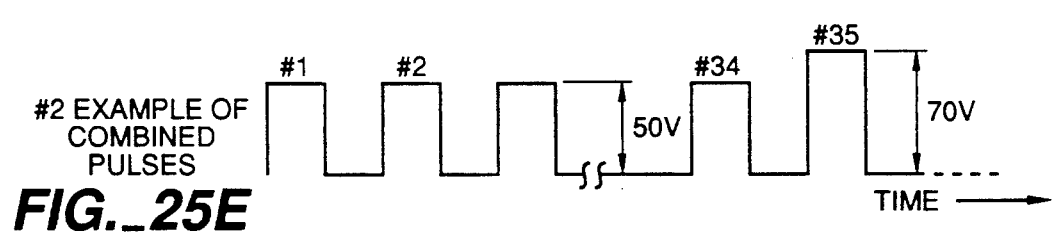
FIG._25E #2 EXAMPLE OF COMBINED PULSES

MICROPUMP SUPERVISORY CONTROL

This is a division, of application Ser. No. 07/644,704 filed on Jan. 23, 1991.

BACKGROUND OF THE INVENTION

The present invention relates to supervisory control methods and apparatus for micropumps, particularly for two valve-type micropumps constructed by means of silicon micro machining techniques.

Two valve-type micropumps, constructed employing silicon micro machining techniques as disclosed, for example, in U.S. patent application Ser. No. 07/599,298 in the name of Hajime Miyazaki et al., filed Oct. 17, 1990, the disclosure of which is hereby incorporated by reference, are capable of precise flow control in trace amounts and, therefore, particularly suited for medical care applications, such as the administration of insulin to diabetics, and chemical analysis. Where such micropumps are intended for medical applications, safety and reliability present important problems. To date there have been proposed no concrete control systems applicable to such micropumps for regulating discharge rates and monitoring clocks.

SUMMARY OF THE INVENTION

It is an object of the present invention to provide a supervisory control method for micropump functions such as annunciations and safety measures.

It is another object of the present invention to provide a micropump supervisory control method which is capable of accurately controlling trace amounts of micropump flow.

In accordance with one aspect of the present invention, a micropump supervisory control method capable of performing at least one discharge annunciation while driving the micropump for a given period of time to deliver a liquid, an alarm annunciation for giving life prediction and life expiration warning alarms and an operation acknowledge sound annunciation for an alarm having a selected sound pattern is provided.

The design is such that a user may be informed of normal or abnormal operation of the micropump control system. For example, when the power source is disconnected, all pumping and other functions are prevented from operation, even in the case where the power source is reconnected to the circuit. Further, if a system reset is applied during pump operation, the micropump operation is terminated. When a micropump is operated, a timer governing micropump lifetime measures the time period worked even when micropump operation is stopped. The product life expectancy is controlled by the timer so that a life prediction is provided at a given time before expiration of the micropump life expectancy and, upon anticipated life expiration, a warning is provided.

According to still another aspect of the present invention, a micropump supervisory control method so designed that a control unit for controlling a micropump includes a CPU and a custom-made IC so as to produce an alarm from each which are shifted in timing so that a faulty condition is communicated even if one of them malfunctions is provided.

According to still another aspect of the present invention, a micropump supervisory control method so designed that potential piezoelectric element variations for driving a micropump are detected so as to monitor the operating condition of the micropump and an alarm sounded to inform the user of a fault is provided.

According to still another aspect of the present invention, a micropump supervisory control method so designed that the number of pulses of a given frequency generated within a given period is controlled in accordance with the unit discharge rate of a micropump due to the driving per pulse applied to a piezoelectric element for pulse driving the micropump whereby the discharge rate of the micropump is controlled by driving the piezoelectric element with a controlled number of pulse signals is provided. Because the discharge rate of the micropump is controlled digitally, it is possible to obtain a control characteristic that makes possible control of trace discharge amounts with a high degree of accuracy. It is also possible to easily construct this control circuit employing a custom-made LSI circuit thereby ensuring fabrication of a product which is small in size, light in weight and low in cost even if the micropump is made of unitary construction.

According to still another aspect of the present invention, a micropump supervisory control method so designed that the pulse frequency generated in accordance with the unit discharge rate of a micropump due to the driving per pulse applied to a driver piezoelectric element is controlled whereby the piezoelectric element is driven by means of driving signals provided by the pulses of the controlled frequency thereby controlling the micropump discharge rate is provided. In this way, the discharge rate of the micropump is controlled to attain a constant value with respect to time thereby ensuring a flow rate control characteristic of the invention which reduces discharge rate ripple.

According to still another aspect of the present invention, a micropump supervisory method so designed that a pulse drive voltage to be generated is controlled in accordance with a piezoelectric element pulse drive voltage versus micropump unit discharge rate characteristic whereby the piezoelectric element is driven by means of driving signals provided by the controlled pulse drive voltage thereby controlling the discharge rate of the micropump is provided. In this way, the discharge rate of the micropump is controlled analogically thereby ensuring more accurate and finer discharge rate control.

Other objects and attainments together with a fuller understanding of the invention will become apparent and appreciated by referring to the following description and claims taken in conjunction with the accompanying drawings.

BRIEF DESCRIPTION OF THE DRAWINGS

FIG. 1 is a diagram showing the concept of a pump control apparatus according to an embodiment of the present invention.

FIG. 2 is a block diagram, showing the hardware construction of the embodiment of FIG. 1.

FIG. 3 is a diagram explaining the functions of the switches in FIG. 2.

FIG. 4 is a diagram for explaining the operating conditions of the control apparatus.

FIGS. 5 and 6 are timing charts showing different sounding patterns for operation acknowledgement purposes.

FIG. 7 is a diagram for explaining the display on the display unit during the period of discharge annunciation.

FIG. 8 is a diagram for explaining the displays on the display unit during the period of alarm annunciation.

FIG. 9 is a diagram for explaining the display on the display unit during the period of operation acknowledge sound annunciation.

FIG. 10 is a timing chart for the sounding pattern during the execution of an operation acknowledge function.

FIG. 11 is a timing chart showing a discharge frequency and its cycle.

FIG. 12 is a diagram for explaining the timer setting operation.

FIG. 13 is a timing chart showing a sounding pattern for life prediction.

FIG. 14 is a timing chart showing a sounding pattern for warning the expiration of life.

FIG. 15 is a characteristic diagram showing the relation between the potential variation and the lapsed time from the positive-going transition of a piezoelectric element drive pulse.

FIG. 16 is a sectional view showing an embodiment of a micropump of the type pulse-driven by a piezoelectric element according to the present invention.

FIG. 17 is a block diagram showing an embodiment of the driving circuit for driving the micropump by means of the piezoelectric element.

FIGS. 18A and 18B are diagrams showing the operating conditions of the embodiment in FIG. 16.

FIG. 19 is a block diagram of a liquid medicine injecting apparatus employing the micropump, showing an exemplary application of the present invention.

FIG. 20 is a block diagram showing an embodiment of a pulse-number control apparatus according to the present invention.

FIGS. 21A–21E are waveform diagrams for explaining the operation of the apparatus in FIG. 20.

FIG. 22 is a block diagram showing an embodiment of a pluse-frequency control apparatus according to the present invention.

FIGS. 23A–23C are waveform diagrams for explaining the operation of the apparatus in FIG. 22.

FIG. 24 is a block diagram showing an embodiment of a piezoelectric element drive voltage control apparatus according to the present invention.

FIGS. 25A–25E are waveform diagrams for explaining the operation of the apparatus in FIG. 24.

DESCRIPTION OF THE PREFERRED EMBODIMENTS

FIG. 1 is a schematic diagram depicting a micropump supervisory control method according to one embodiment of the present invention. A tank 210 containing liquid medication is connected to micropump 10. Micropump 10 is designed so that a voltage applied to a piezoelectric element incorporated therein causes a strain force which serves as a pumping force. Such an arrangement is particularly suited for delivering trace amounts of a liquid over long periods of time. A needle of syringe 208 directs the flow into a body provided from micropump 10. A control apparatus 200 includes control circuit 221, alarm 222 and display unit 206. Driving pulses from control circuit 221 are applied to piezoelectric element 7, shown in FIG. 16, thereby driving micropump 10.

FIG. 2 is a circuit diagram showing construction of control apparatus 200 hardware. Control apparatus 200 includes $IC_2$ 30, control circuit 221 comprising $IC_1$ 31, and forms a piezoelectric element driver and various control circuits.

FIG. 3 illustrates the functions of switches A to D and select switch E which are connected to CPU 30. The various modes in the Figure are set by these switches. It is assumed that the "mode-0" to "mode-3", respectively, represent the following conditions:

Mode-0: The time interval from system resetting up to detection of "L"-"H" at 0PIN terminal, the 0PIN terminal is always at 32 Hz after system resetting.

Mode-1: The time interval from mode-O until switch C is closed.

Mode-2: The time interval from mode-1 until generation of life expiration warning $AL_2$.

Mode-3: The time interval after mode-2.

In addition to switches A to E, a power supply switch PS, shown in FIG. 2, is provided and has the following functions:

(1) A transition from mode-0 to mode-1, i.e. the transition of the OPIN terminal from L to H, is effected.

(2) Mode-1 to mode-3 are disabled, i.e. the transition of the OPIN terminal from H to L.

$IC_2$ 30 and $IC_1$ 31 process such that when the power supply switch PS is changed from the ON state to the OFF state, the apparatus is prevented from functioning even if power supply switch PS is turned on again.

Referring to the operating conditions of control apparatus 200 of FIG. 4, when the L-H transition of the OPIN terminal is detected after the system has been reset, $IC_2$ 30 produces a sound signal. When switch A is closed, i.e. discharge annunciation, driving pulses are generated so that micropump 10 is driven to discharge a given amount. A sound signal is produced upon completion of discharge. A sound signal is produced when switch B is closed, i.e. the alarm annunciation, as well as when switch E is changed over.

Referring to FIG. 5 which depicts an exemplary sound pattern in this latter case, a sound signal is produced at a driving frequency of 4096 Hz for 2 seconds. A sound signal is continuously produced during the period switch D is closed, i.e. the operation acknowledge sound annunciation. FIG. 6 is a timing chart showing an exemplary sound signal produced in such a case.

The discharge annunciation corresponding to the present discharge rate is effected by closing switch A. In this annunciation, driving pulses for one period of the preset discharge rate are applied to piezoelectric element 7 to drive micropump 10.

Referring to FIG. 7, the initial display on the display unit is as shown on the left side of the figure and the display in the course of the discharge annunciation is as shown on the right side. The initial display condition is restored upon completion of the discharge annuciation.

The driving pulses for this annunciation consist of a predetermined number of pulses having a frequency of 1 Hz so that only during this time period is piezoelectric element 7 operated and micropump 10 driven, thereby transporting an injection of fluid from tank 210 through the needle of syringe 208. When this operation is completed, a sound signal is produced in the pattern depicted in FIG. 5.

In response to the closing of switch B, life prediction ($AL_1$) and life expiration ($AL_2$) alarm annunciations are effected. During the time that switch B is closed, an alarm is sounded and, simultaneously, the display is replaced by an alarm display. FIG. 8 is a schematic diagram showing the displays on the display unit in such case. Each time switch B is closed, the sound signal and display (L or E) for life prediction (AL$_1$) or life expiration warning (AL$_2$) are produced cyclically. In this latter case, the respective sounding patterns are the patterns of FIGS. 13 and 14.

When switch D is closed, the operation acknowledge sound annunciation for determining whether the apparatus is operating properly is effected. When the apparatus is functioning properly, an operation acknowledge sound is produced designating normal operation. The operation acknowledge sound is produced as long as switch D is closed. FIG. 9 is a schematic diagram showing the display in this case. The display remains the same as in the initial condition. The resulting sounding pattern is as shown in FIG. 6.

When the apparatus is operating properly in mode-2, including cases where the discharging condition exists and where discharge is stopped, closing switch D produces a signal sound informing a user that the apparatus is operating properly. This determination of whether operation is proper or not is effected by determining whether the operation is passing through the proper loop on the software of IC$_2$ 30 and IC$_1$ 31.

FIG. 10 is a timing chart of the sounding pattern for the operation acknowledge function in such case. When switch D is closed, a sound signal is continuously produced at a frequency of 4096 Hz. The display during sounding is the same as the display during operation.

Setting a discharge rate is accomplished in the following manner. Driving pulse data is inputted in the form of P$_n$ to P$_1$ and basic driving pulses P are set in accordance with the following relationship.

$$P = 10 + (P_8, P_7, P_6, P_5 P_4)$$

For example, if there are inputs in P$_8$ and P$_4$, the above relationship becomes:

$$P = 10 + (1, 0, 0, 0, 1) = 27 \text{ pulses}$$

Here, (P$_3$, P$_2$, P$_1$) represent correction bits and, the following hold:

$$(1, 0, 1) = -3$$

$$(1, 1, 0) = -2$$

$$(1, 1, 1) = -1$$

$$(0, 0, 0) = 0$$

$$(0, 0, 1) = +1$$

$$(0, 1, 0) = +2$$

$$(0, 1, 1) = +3$$

$$(1, 0, 0) = +4$$

The actual number of driving pulses PR including the correction bits, is represented by the following relationship:

$$PR = 10 + (P_8, P_7, P_6, P_5, P_4, P_3, P_2, P_1).$$

For example, the driving pulses could be set as follows:

$$PR = 10 + (1, 0, 0, 0, 1, 0, 1, 1) = 30$$

This discharge rate is adjusted by using the two contacts of switch E so that three states of (0, 0), (0, 1) and (1, 0) are produced and the discharge rate is selectively adjusted to three levels termed LO, MI, and HI. The LO, MI, and HI values are set without fractional portions according to the following relationships:

$$LO: PRL = PR$$

$$MI: PRM = PR \times 11/8$$

$$HI: PRH = PR \times 7/4$$

FIG. 11 is a timing chart showing the discharge frequency and cycle. In this case, a present number of pulses are arranged in the first half of a preselected period of 3 minutes, for example. The preset number of pulses may be uniformly distributed within this period. When the selection of LO, MI, or HI is made, the resulting display on display unit 23 becomes "SEL1", "SEL2", or "SEL3", respectively.

Next, the timer concerning the lifetime of control apparatus 200 will be described. Here, the description will assume that the lifetime of control apparatus 200 is 8 days.

The setting of the timer is effected in the following manner. For instance, when the apparatus is placed in mode 2 after x days since it has been placed in mode-1, the "8-day timer" is reset and the timer is started anew. FIG. 12 is a diagram explaining the operation in such a case. For instance, if mode-2 is started after 0.8 days following the start of mode-1, the "8-INT(x)"-day timer is started. At this time, the display becomes a "day" value for y where (0 < x < 8) and y = 7-INT(x) days.

It is to be noted that INT(x) represents the integer form of x and therefore INT(1.5) = 1, for example. When the number of remaining days becomes or decreases to 1, life prediction AL$_1$ is sounded. Life expiration warning AL$_2$ is sounded when the number of remaining days is zero. In this example, the elapsing of 8 days following the start of mode-2 is required for triggering the sounding of life expiration warning AL$_2$.

When, for example, mode-2 is started 3.2 days after the start of mode-1, the "8-INT(x)"-days timer is started. At this time, the display is in the form of y = 7-INT(3.2) = 4 days. Thus, life prediction AL$_1$ is sounded when the number of remaining days is 1 and life expiration warning AL$_2$ is sounded when the number of remaining days is zero. In this example, a lapse of 5 days following the start of mode-2 is required for triggering the sounding of life expiration warning AL$_2$.

When, for example, mode-2 is started 7.3 days following the start of mode-1, the "8-INT(x)"-day timer is started. At this time, the display indicates y = 7-INT(7.3) = 0 days. Since the number of remaining days is 1, life prediction AL$_1$ is immediately sounded and life expiration warning is sounded when the number of remaining days is reduced to zero. In this example, the lapse of 1 day is required before life expiration warning AL$_2$ is sounded following the start of mode-2. Where x > 8, life expiration warning AL$_2$ is sounded immediately and the apparatus cannot be placed in mode-2.

With life prediction AL$_1$, prediction is effected by the production of a sound signal at the expiration of 7 days after the apparatus has been placed and left in mode-1 as well as at the expiration of 7-INT(x) days after the apparatus has been placed in mode-2 for x days. FIG. 13 is a timing chart showing the sounding pattern in such case. The pattern of this Figure is repeatedly sounded for 30 seconds at a intervals of 30 minutes, and the sounding pattern continues for up to 24 hours unless a stop command is issued. To stop the sounding, switch D is closed so that the sound signal within the current sounding period is interrupted. However, the sound signal is produced upon reaching the next sounding period so that switch D must be closed again, thereby stopping the sound signal again and thereafter no sounding sound is produced even upon reaching succeeding sounding periods.

With life expiration warning $AL_2$, prediction is effected by production of a sound signal at the expiration of 8-INT(x) days after expiration of 8 days with the apparatus placed in mode-1 as well as at the time it is placed in mode-2 after x days. FIG. 14 is a timing chart showing the sounding pattern in such a case. This pattern is repeatedly sounded for 30 seconds at a periodic rate of 30 minutes so that, in the absence of a stop command, the sound signal is produced continuously until the battery voltage drops, thus stopping operation of $IC_2$ 30 or $IC_1$ 31.

To stop the sound signal, switch PS is opened. When switch PS is opened, the 0PIN terminal changes from "H" to "L" so that $IC_2$ 30 detects the change and further detects the L level by the second reading, thereby, stopping the signal sounding. Once the sounding is stopped by switch PS, the sound signal ceases. Even if the discharge operation is stopped for safety purposes in consideration of medication life, the timer is operated without stopping and thus the previously mentioned life prediction $AL_1$ and life expiration warning $AL_2$ are given.

In the present embodiment of the invention, the sounding of buzzer Bz or an alarm is effected by $IC_2$ 30 and $IC_1$ 31. In any of the cases including the sounding patterns of FIGS. 13 and 14, the sound signal is produced by turning on transistor T, shown in FIG. 2, thereby driving buzzer Bz. Buzzer Bz is driven by $IC_2$ 30 and $IC_1$ 31, shifted in timing from each other so that even if CPU 30 or control circuit 31 malfunctions, a user is so informed.

In connection with the safety mechanism of control apparatus 200, the state of terminal $V_{DE}$ is read at times $T_1$, $T_2$ and $T_3$ from the leading edge of the first piezoelectric element driving pulse at each period, e.g. 3 minutes, of driving pulses generated from terminal $VDR_1$ of FIG. 2. In circumstances where the values are other than $(T_1, T_2, T_3) = (0, 1, 1)$, respectively, the state of terminal $V_{DE}$ is read as previously mentioned at the leading edges of the corresponding two piezoelectric element driving pulses, whereby a sound signal is produced in the same sounding pattern as the life expiration warning $AL_2$, hereinafter referred to as alarm $AL_2$.

FIG. 15 is a characteristic diagram showing the relation between the potential variation at terminal $V_{DE}$ and the time interval from the leading edge of the piezoelectric element driving pulse. Assuming that $T_1 = 10$ ms, $T_2 = 30$ ms and $T_3 = 50$ ms, a comparison between the potentials at these time intervals and the threshold value shows that (0, 1, 1) results under normal conditions. When air is introduced into the micropump, the potential at terminal VDE rises rapidly and a comparison between the resulting potential and the threshold value produces the values (1, 1, 1). When the point of the needle of syringe 208 is clogged, the potential at terminal $V_{DE}$ rises slowly so that a comparison between the resultant potentials and the threshold value results in (0, 0, 0).

The potential variations of the piezoelectric element are detected to determine whether operation of the micropump is proper or improper, so that when operation is improper, switch PS can be opened to stop operation and the micropump replaced.

On the other hand, the voltage of battery VE is monitored at all times so that if the battery output-voltage, having a rated voltage of 3 V, drops, for example to 2.4–2.5 V, the drop is detected and alarm $AL_2$ is sounded. When a system reset is applied while the micropump is being carried by a user including cases where it is caused by noise, the potential at terminal OPIN is read to discriminate between L and H levels so that if the potential is for example at the H level, it is considered that the micropump is malfunctioning and alarm $AL_2$ is sounded. In any case, when alarm $AL_2$ is sounded, control apparatus 200 stops operation thereby ensuring user safety.

A micropump embodiment adapted to be pulse driven by a piezoelectric element will now be described and the method of controlling the discharge rate of the micropump through pulse driving of the piezoelectric element will also be described.

In FIG. 16, a micropump 10, pulse-driven by a piezoelectric element according to the present invention, includes a sandwich structure having base 1, thin-film sheet 2, and surface sheet 3.

Base 1 comprises, for example, a glass base of about 1 mm thick and formed with inlet port 11 and outlet port 12. Tubes 13 and 14 are fitted on ports 11 and 12, respectively, with adhesive 15 providing a fluid-tight seal. The base end of tube 13 is connected, for example, to liquid medicine tank 210 and the forward end of tube 14 is connected, for example, to syringe 208.

Thin-film sheet 2 comprises a silicon substrate of about 0.3 mm thick and forming, by an etching process, inlet valve 4, outlet valve 5, diaphragm 6 interposed between the valves, and any necessary flow passages, not shown. Sheet 2 is typically bonded onto base 1 employing anodic bonding at bonding positions 16a, 16b, 16c.

Inlet port 11 is connected to an input passage, not shown. The input passage communicates via a through-hole, not shown, with chamber 113 disposed above outlet valve 5 and also communicates with chamber 116 of inlet valve 4 through another through-hole and passage, not shown. Inlet valve 4 is formed with valve member 41 having through-hole 117 in a central portion and communicates with chamber 118 disposed above. Chamber 118 communicates through still another through-hole and passage, not shown, to pump chamber 121 below diaphragm 6. Pressurized liquid flows into chamber 123 of outlet valve 5 through an output passage. Outlet valve 5 is formed by cap-shaped valve member 51 which covers inlet 12a of outlet port 12.

Piezoelectric element 7, the driving means of diaphragm 6, comprises a piezoelectric disc secured to diaphragm 6 through a thin-film electrode. Lead wires 2 and 73 are used to apply a voltage to piezoelectric element 7.

Surface sheet 3, composed of a glass substrate similar to base 1, is bonded by anodic bonding onto thin-film sheet 2 so as to form an insertion opening 31 for piezoelectric element 7, thereby establishing the pump flow passage system. Surface sheet 3 has a thickness of about 0.5 mm.

FIG. 17 is a block diagram depicting a circuit for driving the micropump with the piezoelectric element.

This exemplary embodiment includes power source 201, e.g., a lithium cell, a booster circuit 202, a microprocessor 203 (hereinafter referred to as a CPU), a level shifter 204 for converting a low-voltage signal to a high-voltage signal, a driver 205 for driving piezoelectric element 7, a pump flow rate indicator 206, and a flow rate control selector switch 207.

Referring to FIGS. 17, 18A, and 18B depicting the ordinary operation of the micropump of FIG. 16, the desired flow rate is first selected by switch 207. Pump driving pulse signals are generated from CPU 30. Signals from CPU 30 are generally activated by a voltage of 3 to 5 V and piezoelectric element 7 is operated at a high voltage, typically 50 V. The input voltage of 3 V is increased to 50 V by booster circuit 202 and the pulse signals from CPU 203 are converted to high-voltage pulse signals of 50 V.

Driver 205 applies periodic driving signals of 50 V at about 1 to several $H_z$ to piezoelectric element 7 with the resulting piezoelectric effect causing strain vibrations. When the strain vibrations deform diaphragm 6, as shown in FIG. 18A, pressure in pump chamber 121 is increased and transmitted through flow passages to chambers 118 and 123, thereby increasing their internal pressure. With the increase in internal pressure of chamber 118, partition wall 42, formed with inlet valve 4, is forced downward so that valve member 41 of inlet valve 4 is pressed against base 1 and inlet valve 4 is closed. The increase in the internal pressure of chamber 123 forces partition wall 52 upward so that valve member 51 of outlet valve 5 is separated from base 1 and outlet valve 5 is opened thereby discharging a fixed amount of pressurized liquid to outlet port 12.

When diaphragm 6 is deformed upward, as shown in FIG. 18B, the internal pressure of pump chamber 121 is decreased and partition wall 52 of chamber 123 is deformed downward, thus closing outlet valve 5. Partition wall 42 of chamber 118 is deformed upward thus opening inlet valve 4, thereby drawing a fixed amount of liquid from chamber 116, in communication with inlet port 11, through through-hole 117.

By causing diaphragm 6 to vibrate through piezoelectric element 7, filling suction and discharge are continuously effected. The increased number of vibrations reduces pump ripple. Since outlet valve 5 is formed by cap-shaped valve member 51 which covers inlet 12a of outlet port 12, the direction of application of the lifting force of partition wall 52 due to the back pressure of outlet port 12, i.e. the opening force of outlet valve 5, is the same with the direction of upward movement of partition wall 52 due to the pressure in pump chamber 121. Therefore, back pressure acts in a direction tending to open outlet valve 5. As a result, liquid is discharged at a substantially fixed flow rate until back pressure overcomes the resilient force of outlet valve 5 and the urging force acting on partition wall 52 due to an external force within a desired working range of the pump.

In micropump 10 according to the present embodiment, when a driving pulse of 50 V, for example, is applied once to micropump piezoelectric element 7, referred to as single-pulse driving or single-step driving, the liquid is discharged at a flow rate of about 0.05 μl/step.

In the exemplary liquid medicine injecting apparatus depicted in FIGS. 16 and 19, tube 13 provides fluid communication between medicine tank 210 and inlet port 11 of micropump 10, tube 14 between outlet port 12 of the micropump and syringe 208 for injecting liquid medication into a living body, and discharge rate control apparatus 400 including the micropump driving circuit of FIG. 17.

Referring to FIGS. 20, 21 and 22, a specific embodiment of discharge rate control apparatus 400 will be described in detail to explain the micropump discharge rate control methods. Micropump discharge rate control methods are broadly divided into the following four types:
(1) Pulse number type;
(2) Pulse frequency type;
(3) Piezoelectric element driving voltage control type;
(4) The method of (1) or (2) and the method of (3).

FIG. 20 is a block diagram showing an embodiment of a pulse-number type control apparatus constructed according to the present invention having fixed setting means 401, adder 402, and basic setting means 403 capable of setting any given 5-bit binary number (0 to 31) through switches $S_8$ to $S_4$. Adder/subtractor means 404 and fine adjustment setting means 405, which are capable of setting any number ranging from −3 to +4 through the on and off operation of switches $S_3$ to $S_1$, are also shown. #1 coefficient multiplier 406 multiplies input data by a coefficient $K_1$ of, 11/8 here set equal to, generate an output. #2 coefficient multiplier 407 multiplies input data by a coefficient $K_2$, 7/4 here set equal to, to generate an output. A selector 408 selects one of three input signals in accordance with the output signals of switches $S_a$ and $S_b$. A pulse generator 409 is responsive to the application of a trigger signal to count clock signals and thereby generate a predetermined number of pulse signals. This circuit may also be formed by a down counter, a flip-flop, an AND gate or the like.

Operation of the apparatus of FIG. 20 will be described with reference to FIG. 21. Assume that a fixed number "10" has been preliminarily set in fixed setting means 401. Any given 5-bit binary number n, where n is a number between a minimum of 0 and a maximum of 31, is set in basic setting means 403 through the on and off operation of switches $S_8$ to $S_4$. Adder 402 adds the number "10" from fixed setting means 401 and number n from basic setting means 403 to produce a number "n+10" which is between a minimum of "10" and a maximum of "41".

When switches $S_3$ to $S_1$ are turned on, fine adjustment setting means 405 goes to a "1" level causing application of power supply voltage $V_{cc}$. When switches $S_3$ to $S_1$ are turned off, fine adjustment setting means 405 goes to a "0" level so that supply voltage $V_{cc}$ is not applied. Thus, depending on the set data of switches $S_3$, $S_2$ and $S_1$, a corresponding numerical value ranging from −3 to +4 is set as follows:

| Data Set ($S_3$, $S_2$, $S_1$) | Set Value |
| --- | --- |
| 1, 0, 1 | −3 |
| 1, 1, 0 | −2 |
| 1, 1, 1 | −1 |
| 0, 0, 0 | −0 |
| 0, 0, 0 | 1 |
| 0, 1, 0 | 2 |
| 1, 1, 1 | 3 |
| 1, 0, 0 | 4 |

Adder/subtractor means 404 performs addition or subtraction on the value n+10 from adder 402 and the fine adjustment number, i.e. the number between "−3" and "+4", so that the result of the calculation is supplied directly as a #1 input signal to selector 408 and also supplied to #1 coefficient multiplier 406 and to #2 coefficient multiplier 407. Multiplier 406 multiplies input data by the coefficient $K_1$, "11/8" here set equal to, so that fractions are omitted and the resulting integral output data is supplied as a #2 input signal to selector 408. Multiplier 407 multiplies the input data by the coefficient $K_2$ here having a value of "7/4" so that fractions are similarly omitted and the resulting integral output data is supplied as a #3 input signal to selector 408.

Selector 408 performs a selection operation, as shown below, in accordance with the data selected by switches $S_a$ and $S_b$. The selector 408 output signal is supplied as a pulse-number command data to pulse generator 409. The operations selected by switches $S_a$ and $S_b$ are set as follows:

| Data Set ($S_a$, $S_b$) | Selection Operation |
|---|---|
| 0, 0 | None of the input signals is outputted. |
| 0, 1 | The #1 input signal is selected and outputted. |
| 1, 0 | The #2 input signal is selected and outputted. |
| 1, 1 | The #3 input signal is selected and outputted. |

FIGS. 21A and 21B depict waveforms of clock signals and trigger signals, respectively, supplied to pulse generator 409. The clock signals consist of repetition pulses having a period t, e.g. 1 second, and having the same on and off times, e.g. the duty cycle is 50%. The trigger signal is a periodic signal of period T which is generated each time a given number of clock signals are counted, e.g. the time T required for counting 180 clock signals having a frequency of 1Hz is 3 minutes.

When the pulse-number command data is supplied, pulse generator 409 presets the pulse-number command data in the counter which, for example, is incorporated therein. Then, when the trigger signal is applied, the generation of clock signals is initiated and subtraction of "1" is effected for every clock signal. When the preset count is reduced to zero, the generation of subsequent clock signals is inhibited. This operation is repeated in response to the application of each trigger signal. In this way, the commanded number of pulse signals are generated in response to the application of each trigger signal.

FIG. 21C depicts the waveform of low-number pulses when the #1 input signal from adder/subtractor means 404 is selected by selector 408. FIG. 21D depicts the waveform of medium-number pulses when the #2 input signal from #1 coefficient multiplier 406 is selected by selector 408. FIG. 21E depicts the waveform of high-number pulses in the case where #3 input signal from #2 coefficient multiplier 407 is selected by selector 408.

Employing the apparatus of FIG. 20, a given number of pulses ranging from a minimum of 7 (10+0−3) to a maximum of 45 (10+31+4) in the case of low number pulses, from a minimum of 9 to a maximum of 61 in the case of medium-number pulses and from a minimum of 12 to a maximum of 72 in the case of high-number pulses are generated within the period T, e.g. 3 minutes in the previous example, of the trigger signal. These pulse signals are supplied to level shifter 204 in the piezoelectric element driving circuit of FIG. 17. Level shifter 204 converts the input pulse signals to high voltage pulse signals, for example 50V thereby driving piezoelectric element 7 through driver 205. The micropump discharges the liquid in response to displacement of diaphragm 6 operatively associated with piezoelectric element 7. The discharge rate of the micropump is controlled in accordance with the pulse number representing the number of pulses within a given period.

FIG. 22 is a block diagram showing an embodiment of a pulse frequency type control constructed according to the teachings of the present invention. Numerals 401–408 designate the same devices shown in FIG. 20. D/A convertor 501 for converting digital data to analog voltage and voltage-to-frequency (V/F) convertor 502, whose oscillation frequency is controlled by an input control voltage are also shown.

Referring to FIG. 23, devices 401 to 408 of FIG. 22 are operated in substantially the same manner as their counterparts in FIG. 20. In FIG. 20 the operation of determining the number of pulse signals of period t within the overall period T is performed.

With the apparatus of FIG. 20, however, it will be seen that there are operating periods when clock pulse signals of period t are continuously generated immediately following application of the trigger signal and the rest period where no clock pulse signals are generated. In the apparatus of FIG. 22, the oscillation frequency of V/F converter 502 is controlled so that the rest period of generating no pulse signals is reduced to a minimum or zero. Control is effected to maintain a constant discharge rate with respect to the time base, thereby reducing discharge rate ripple. As a result, data set in fixed setting means 401, basic setting means 403 and fine adjustment setting means 405 relate to frequencies.

Selector 408 selects one of three frequency command data and supplies that selection to D/A convertor 501. Convertor 501 supplies an analog control voltage corresponding to the input data to V/F convertor 502. Convertor 502 generates signals of an oscillation frequency controlled by the input control voltage as pulse signals subjected to waveform reshaping.

FIGS. 23A, 23B and 23C depict waveforms of low-frequency pulses, intermediate-frequency pulses and high-frequency pulses, respectively. If the frequency of high-frequency pulses is represented by f, the frequency of intermediate-frequency pulses is represented as f/2 and the frequency of the low-frequency pulses is represented as f/3. However, it should be noted that frequency f is on the order of 1 Hz to several tens of Hz and thus lower than the frequency of the AC power supply and differs from the frequency used in accordance with the ordinary frequency classification.

According to an alternative method, there is provided a frequency divider circuit having a variable frequency dividing ratio in place of D/A convertor 501 and V/F convertor 502 whereby clock signals of a relatively high frequency are first generated and the clock signals are subjected to frequency division by a desired frequency dividing ratio to produce a lower frequency, thereby digitally generating signals of any desired frequency.

In the driving voltage type control method for a piezoelectric element, the pulse driving voltage applied to piezoelectric element 7 is continuously varied in a range, for example, of 30 V to 100 V. The displacement due to the piezoelectric effect of the piezoelectric element is correspondingly varied. It is therefore possible to control the discharge rate of the micropump by utilizing the piezoelectric effect. In general, the voltage range that can be applied to piezoelectric element 7 to produce the piezoelectric effect is not wide. However, it is possible to effect fine analog control within this variable range.

Each pulse number-type control method and pulse frequency-type control method is a digital control method. Therefore control of the discharge rate per fraction of a pulse cannot be performed. Thus, the pulse number-type control method cannot control the discharge rate corresponding, for example, to 35.6 pulses per 3 minutes. The piezoelectric element driving voltage control method includes a feature for making such control possible. Moreover, the control method of the piezoelectric element driving voltage control type can be performed singly or in combination with other control methods of the pulse-number type or the pulse-frequency type.

FIG. 24 is a block diagram showing an embodiment of a piezoelectric element driving voltage control apparatus according to the teaching of the present invention. D/A convertor 601 converts externally supplied voltage control data, e.g. supplied by voltage control data command means formed by devices identical to devices 401–408 of FIG. 20, to an analog control voltage and booster circuit 602 increases the voltage whereby a DC power source is subjected to DC/DC conversion to a high voltage. The circuit is responsive to an external control voltage to control the duty cycle of DC/DC conversion pulses and thereby variably control output voltage within a range, for example, of 30–100 V. A pulse generator 603 is included for generating pulse signals of a given frequency from an internal oscillator when a switch $S_c$ is open and for generating pulse signals corresponding to the pulse-number or pulse-frequency control signal supplied externally when the switch $S_c$ is closed. A driving circuit 604, responsive to the pulse signals from pulse generator 603, applies the controlled voltage from booster circuit 602 to piezoelectric element 7.

FIGS. 25A–25E are waveform diagrams depicting the operation of the apparatus in FIG. 24. FIG. 25A depicts a piezoelectric element driving waveform for low voltage pulses, e.g. 30 V, of a given frequency. FIG. 25B is a similar driving waveform diagram for medium-voltage, e.g. 50 V, pulses of given frequency. FIG. 25C is a similar driving waveform for high-voltage, e.g. 100 V, pulses of given frequency.

FIGS. 25D and 25E are examples of waveforms provided by the combined control of the pulse number-type control and the piezoelectric element driving voltage-type control. FIG. 25D depicts a case in which in order to control, for example, a discharge rate corresponding to 35.6 pulses within the previously mentioned case of 3 minutes, the piezoelectric element is driven by #1 to #35 pulses at a voltage of 50 V and by #36 pulse alone at a voltage of 30 V and finally the small discharge rate corresponding to 0.6 pulse is added. As shown in FIG. 25E, in order to control the discharge rate corresponding to 35.4 pulses within 3 minutes, the piezoelectric element is driven by #1 to #35 pulses at 50 V and by #35 pulse alone at 70 V and finally the discharge rate corresponding to 1.4 pulses is added. By so doing, highly accurate discharge rate control can be obtained.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A supervisory control method for a piezoelectric element driven micropump which has a predicted maximum useful operating lifetime comprising, the steps of:
producing a discharge annunciation while driving a micropump;
producing life-prediction when said micropump has been operated for a period of time less than said predicted lifetime, and life-expiration warning alarm annunciation when said micropump has been operated for said predicted lifetime; and
producing an operation acknowledge alarm having a predetermined sounding pattern when it is determined that said micropump is operating properly.

2. The supervisory control method according to claim 1, further comprising the step of inhibiting all micropump functions when a power source is reconnected.

3. The supervisory control method of claim 2 further comprising the step of measuring the operating time of the micropump beginning with when it is first driven through any periods of interrupted operation.

4. The supervisory control method of claim 3 further comprising the steps of providing a first IC and a second IC, each IC being adapted to produce at least one of said warning alarms which is output in a time shifted manner from each IC relative to the other.

5. The supervisory control method of claim 4 wherein each of said first and second ICs are configured to produce both said life-prediction and life-expiration alarms.

6. The supervisory control method of claim 4 wherein each of said first and second ICs are configured to produce one of said life-prediction and life-expiration alarms.

7. The supervisory control method of claim 4 further comprising the step in detecting potential variations in the piezoelectric element so as to monitor the micropump operating condition.

8. The supervisory control method of claim 1 further comprising the step of controlling the number of pulses of predetermined frequency generated within a predetermined period whereby the piezoelectric element is single-pulse driven by driving signals provided by said controlled number of pulses, thereby controlling the discharge rate of the micropump.

9. The supervisory control method of claim 1 further comprising the step of controlling a frequency of generated pulses whereby a single-pulse driven piezoelectric element is driven by driving signals provided by pulses of said controlled frequency thereby controlling the discharge rate of said micropump.

10. The supervisory control method of claim 1 further comprising the step of controlling a single-pulse driving voltage signal to the piezoelectric element thereby controlling the discharge rate of said micropump.

11. The supervisory control method of claim 1 wherein said life-prediction warning alarm is produced at preselected intervals after said micropump is operated for a length of time which precedes said predicted lifetime by a preselected amount.

12. The supervisory control method of claim 11 wherein said life-prediction warning alarm is generated in response to micropump operator interrogation.

13. The supervisory control method of claim 12 further comprising the step of activating a life-prediction interrogation means connected to said micropump for determining if said preselected amount of time has been reached.

14. The supervisory control method of claim 11 further comprising the step of terminating said life-prediction warning alarm annunciation in response to a micropump user command.

15. The supervisory control method of claim 14 further comprising the step of activating an alarm termination switch.

16. The supervisory control method of claim 11 further comprising the step of automatically terminating said life-prediction warning alarm after a preselected time interval.

17. The supervisory control method of claim 1 wherein said life-expiration warning alarm is produced at preselected intervals after said micropump is activated for use.

18. The supervisory control method of claim 17 wherein said life-expiration warning alarm is generated in response to micropump operator interrogation.

19. The supervisory control method of claim 18 further comprising the step of activating a life-expiration interrogation means connected to said micropump for determining if said lifetime has been reached.

20. The supervisory control method of claim 19 further comprising the step of activating an alarm termination switch.

* * * * *